US010228470B2

United States Patent
Wu et al.

(10) Patent No.: US 10,228,470 B2
(45) Date of Patent: Mar. 12, 2019

(54) METHOD AND SYSTEM FOR REAL-TIME PROCESSING OF PULSE PILE-UP EVENT

(71) Applicant: RAYCAN TECHNOLOGY CO., LTD. (SU ZHOU), Suzhou (CN)

(72) Inventors: Xiaoke Wu, Suzhou (CN); Jun Zhu, Suzhou (CN); Ming Niu, Suzhou (CN); Tong Liu, Suzhou (CN); Qingguo Xie, Suzhou (CN)

(73) Assignee: RAYCAN TECHNOLOGY CO., LTD. (SU ZHOU), Suzhou (CN)

( * ) Notice: Subject to any disclaimer, the term of this patent is extended or adjusted under 35 U.S.C. 154(b) by 0 days.

(21) Appl. No.: 15/773,997

(22) PCT Filed: Nov. 4, 2016

(86) PCT No.: PCT/CN2016/104499
§ 371 (c)(1),
(2) Date: May 4, 2018

(87) PCT Pub. No.: WO2017/076312
PCT Pub. Date: May 11, 2017

(65) Prior Publication Data
US 2018/0321391 A1     Nov. 8, 2018

(30) Foreign Application Priority Data
Nov. 5, 2015  (CN) .......................... 2015 1 0751817

(51) Int. Cl.
*G01T 1/161*     (2006.01)
*G01T 1/164*     (2006.01)
(Continued)

(52) U.S. Cl.
CPC ............ *G01T 1/1642* (2013.01); *G01T 1/161* (2013.01); *G01T 1/164* (2013.01); *G01T 1/1648* (2013.01);
(Continued)

(58) Field of Classification Search
CPC ....... A61B 6/037; G01T 1/1647; G01T 1/247; G01T 1/161; G01T 1/164; G01T 1/1648; G01T 1/2006; G01T 1/248; G01T 1/29
See application file for complete search history.

(56) References Cited

U.S. PATENT DOCUMENTS 6,252,232 B1 *   6/2001   McDaniel ............. G01T 1/1647
                                                250/363.02
2007/0069140 A1  3/2007   Arseneau

FOREIGN PATENT DOCUMENTS

CN     1511266      7/2004
CN     104101894   10/2014
(Continued)

OTHER PUBLICATIONS

Lewellen et al., "Evaluation of a Clinical Scintillation Camera with Pulse Tail Extrapolation Electronics," The Journal of Nuclear Medicine, p. 1554-1558, published 1989.
(Continued)

*Primary Examiner* — David P Porta
*Assistant Examiner* — Fani Boosalis
(74) *Attorney, Agent, or Firm* — Arent Fox LLP

(57) ABSTRACT

A method for real-time processing of a pulse pile-up event comprises the following steps of: generating a fitted baseline value lookup table and a fitted energy value lookup table for a pulse falling edge, using a multi-voltage threshold sampling method to identify piled-up pulses and trigger a procedure of processing pulse signals; and using pulse priori information and acquired pulse information to acquire information of an incorrectly sampled portion due to a pulse pile-up by looking up in the tables, so as to recover information of the pile-up pulses in real time. First, in the disclosure the multi-voltage threshold sampling method is proposed to identify pile-up pulses at a high count rate and trigger a procedure of processing pulse signals. Next, pulse
(Continued)

priori information and acquired pulse information are used to acquire information of an incorrectly sampled portion due to a pulse pile-up by looking up in the tables, to recover information of the piled-up pulses in real time. The method according to the disclosure is simple, highly efficient, can be realized easily in a real-time data acquisition system of a detector level, and is still capable of achieving a preferable effect of recovering formation of piled-up pulses at a low sampling rate.

7 Claims, 5 Drawing Sheets

(51) Int. Cl.
*G01T 1/29* (2006.01)
*G01T 1/20* (2006.01)
*G01T 1/24* (2006.01)
*A61B 6/03* (2006.01)
(52) U.S. Cl.
CPC ............ *G01T 1/2006* (2013.01); *G01T 1/248* (2013.01); *G01T 1/29* (2013.01); *A61B 6/037* (2013.01)

(56) References Cited

FOREIGN PATENT DOCUMENTS

| CN | 104586414 A | 5/2015 |
| CN | 105212954 | 1/2016 |

OTHER PUBLICATIONS

Wang et al., "Advantages of Digitally Sampling Scintillation Pulses in Pileup Processing in PET," IEEE Nuclear Science Symposium Conference Record, p. 144-147, published 2009.
Deng et al., "Scintillation Event Energy Measurement Via a Pulse Model Based Iterative Deconvolution Method," Physics in Medicine & Biology 58, p. 7815-7827, published Oct. 21, 2013.
Li et al., "A New Statistics-Based Online Baseline Restorer for a High Count-Rate Fully Digital System," IEEE Trans Nuclear Science, published May 18, 2010.
Xie, Qingguo et al., "Potentials of Digitally Sampling Scintillation Pulses in Timing Determination in PET," IEEE Translations on Nuclear Science, vol. 56, No. 5, dated Oct. 31, 2009, pp. 2697-2613.
International Search Report for PCT/CN2016/104499 dated Jan. 6, 2017.

* cited by examiner

METHOD AND SYSTEM FOR REAL-TIME PROCESSING OF PULSE PILE-UP EVENT

CROSS REFERENCE TO RELATED APPLICATIONS

This application is a U.S. National Stage Application under 35 U.S.C. § 371 of International patent application Ser. No. PCT/CN2016/104499, filed Nov. 4, 2016, entitled "METHOD AND SYSTEM FOR REAL-TIME PROCESSING OF PULSE PILE-UP EVENT," which claims the priority of CN application No. 201510751817.7, entitled "METHOD AND SYSTEM FOR REAL-TIME PROCESSING OF PULSE PILE-UP EVENT" filed with the SIPO on Nov. 5, 2015, of which the entire contents have been incorporated herein and herewith by reference.

BACKGROUND

Field

The disclosure relates to the field of digital signal processing, specifically to a method and system for real-time processing of a pulse pile-up event based on the multi-voltage threshold sampling technique.

Background

In the fields of high-energy particle detection and of nuclear medicine imaging such as Positron Emission Tomography (abbr.PET), detection of information of gamma photons is needed. Usually, gamma photons are converted into visible light photons using a scintillation crystal, and then into scintillation pulse electrical signals using a photoelectric conversion device, and finally the corresponding gamma photon information contained in the scintillation pulse electrical signals are extracted by a data acquisition circuit.

Count performance is one of the basic performance indicators of high-energy particle detectors, indicating the limit of event counts that the system can acquire in a unit interval. In high-activity and high-sensitivity demanding nuclear medicine imaging applications such as high-radiation flux cosmic ray detection and short-lived radiotracers, dynamic scanning, etc., high requirement for the count performance limit of the high-energy particle detectors is put forward.

As the count rate of detector increases, the pile-up phenomenon of the scintillation pulse becomes more serious and constitutes the main cause that affects the performance and the count limit of detectors. A pulse pile-up is defined as detection of more than two gamma photon events in the same detection channel for a duration of one scintillation pulse. The pulse pile-up causes the waveforms of multiple scintillation pulses to overlap, and affects the independent acquisition of information for each scintillation pulse by the data acquisition system, which will cause a series of issues such as count loss, and deterioration of energy information and of position information, thereby seriously degrading the performance of the detectors at a high count rate.

To address the issues of deterioration of the detector performance caused by a pulse pile-up at a high count rate, various methods have been proposed by researchers, such as the dynamic integration method-detecting the time interval between two triggered pulses; if a second pulse arrives within one integration time, terminating integration of the first pulse, and estimating the non-integrated portion of the first pulse with a pulse model; adding the estimated value to the integral value of the first pulse, and subtracting the estimated value from the integral value of the second pulse to finally obtain the actual integral values of the two pile-up pulses. See [1].

The Digital Single Event Reconstruction (abbreviated as DiSER) method has been proposed in [2], which can be seen as an improvement to the dynamic integration method. The DiSER method recovers information of a single pulse in a pile-up event based on a scintillation pulse model. The pulse model consists of a rising edge that rises sharply and a falling edge that decays exponentially. The DiSER method determines the number of scintillation pulses and the interval between occurrence timings by deriving a sampled frame of a digital pulse waveform. A sampled point between the rising edges of the two scintillation pulses is considered to be the falling edge of the previous pulse and is used to reconstruct its entire falling edge, and the falling edge is subtracted when the waveform of the subsequent scintillation pulse is calculated to recover the actual waveform of each pulse in the pile-up event.

Another idea is to treat the gamma photon that enter a detector as an impulse function, while the detector as a black box system which is accordingly configured to comprise a specific system's response function, such that the scintillation pulse electrical signals output by the detector to electronics are treated as the convolution result of the impulse function and the system's response function. Due to the existence of noise, the original pulse cannot be solved analytically, and an iterative method may be introduced to recover information of gamma photons from the scintillation pulse electrical signals. Since the detector is regarded as a whole system, the method is not limited by specific pulse shapes in terms of operation principles. Besides, because the duration of the recovered pulse is rather short, it is suitable for a detector with a extremely high count rate. See [3].

Other studies deal with the baseline drift caused by the pulse pile-up. For example, for the baseline drift problem caused by a pile-up, it has proposed in [4] a method of statistically analyzing baseline value distribution: White noise of a circuit accords with the Gaussian distribution and trailing of scintillation pulses accords with the position distribution. Taking into account that points free from influence of the pulse tailing are still of the majority of entire waveform sampled by the analog-to-digital converter (ADC) even at high activity, that is, the Gaussian peak formed by the pulse-free baseline can be identified from the statistical distribution of the baseline value, and the mean value of the Gaussian peak is the current baseline value. Thus, the current baseline value can be tracked and fed back to a pulse sampling end for baseline calibration by updating in real time a baseline database of the baseline portion in ADC sampled waveforms and statically analyzing its amplitude distribution.

When the dynamic integration method and the DiSER method are applied to position-sensitive detectors, they will face the problem of synchronized processing of multiple homologous scintillation pulse signals generated by a gamma photon event. For example, a position-sensitive Photomultiplier Tube (abbreviated as PMT) will generate a group of angular pulse signals containing position information after receiving gamma photons, and the angular pulse signals in the same group are different in waveform. Using the above methods may cause only part of the pulses to be triggered and be subject to subsequent processing. Besides, each angular pulse signal is triggered independently, causing the trigger time to be asynchronous, deteriorating the acquisition accuracy of energy and position information. In addition, the above two methods need to complete acquisition of data frames for a certain length of time and then perform data playback to determine the occurrence time of the pulse pile-up, failing to perform real-time processing of the pile-up pulse in the detector.

The method of recovering pulses using the detector system's response function and the iterative algorithm has higher requirements on the sampling rate during the digital scintillation pulse process, and the iterative algorithm takes more time, leading to difficulties in implementing the method in the detectors and systems which require real-time processing.

The baseline updating process of the pulse pile-up baseline drift processing method based on the pulse baseline value statistics requires a response time, and therefore can only mitigate the baseline drift influence caused by the trailing of the pulse, but cannot recover the pulse in real time when a pulse pile-up occurs.

Therefore, in view of the above technical problems, it is proposed to provide an improved method for real-time processing of a pulse pile-up to overcome the above drawbacks.

SUMMARY

In view of the above, the object of the disclosure is to provide a method for real-time processing of a pulse pile-up event based on the Multi-voltage Threshold (abbreviated as MVT) technique. The method is simple and efficient, easy to be implemented on a real-time data acquisition system of a detector level, and can achieve a preferable effect of recovering piled-up pulse information at a low sampling rate.

To achieve the above object, in the disclosure the following technical solution is provided:

A method for real-time processing of a pulse pile-up event, comprising steps of:

S1: acquiring a digital waveform database of non-pile-up pulses, generating a digital waveform lookup table of pulse falling edges, and storing the same in a data acquisition system;

S2: during data acquisition of pulses containing pile-up pulses, using a multi-voltage threshold sampling method to identify the pile-up pulses and trigger a procedure of processing pulse signals; and S3: during the procedure of processing pulse signals, based on the acquired information of a non-pile-up portion of the pulses looking up the digital waveform table to acquire information of an incorrectly sampled portion due to the pulse pile-up so as to process the pile-up pulses in real time.

In the aforesaid method for real-time processing of a pulse pile-up event, preferably, the step S1 comprises steps of:

P1 in the case of non-pile-up pulses, using the multi-voltage threshold sampling method as a trigger signal of acquiring normal pulses;

P2 after triggering, sampling the pulse waveforms by an Regular-time sampling (abbreviated as RTS) method to acquire scintillation pulse digital waveforms;

P3 extracting amplitude variation of falling edge of each scintillation pulse in a database of scintillation pulse digital waveforms, and generating a respective lookup table of fitted baseline values and a respective lookup table of fitted energy values; and P4 storing the tables in the data acquisition system.

In the aforesaid method for real-time processing of a pulse pile-up event, preferably the step S2 comprises steps of:

P1 acquiring scintillation pulse electrical signals at a high count rate by the data acquisition system, two or more of the scintillation pulses that are excessively adjacent to each other being subject to a pulse pile-up due to a duration of the scintillation pulses and their indefinite occurrence time;

P2 sampling the scintillation pulse electrical signals respectively by an MVT method that performs a voltage comparison of sharply rising edges of the scintillation pulse waveforms with a plurality of voltage thresholds, wherein no matter whether the pulses are pile-up pulses or not, level switching signals can be acquired at the rising edges thereof; and P3 using the level switching signals acquired by the MVT method as identification signals for the pulses to trigger sampling of the pulses with an RTS method and digital integration of the pulses to acquire energy information of the pulses.

In the aforesaid method for real-time processing of a pulse pile-up event, preferably the step S3 comprises steps of:

a. during sampling data at the high count rate by the data acquisition system, in case of occurrence of a pile-up event, using a previous MVT trigger signal as a start signal for digital integration of a previous pulse;

b. upon occurrence of a second MVT trigger signal, looking up the lookup table of fitted energy values using the pulse falling edge of the non-pile-up portion of the previous pulse in the pile-up pulses as an input parameter to acquire an energy value of the pile-up portion of the previous pulse, and adding the latter to the acquired energy value of the non-pile-up portion as an energy value of the previous pulse;

c. meanwhile looking up the lookup table of fitted baseline values using the pulse falling edge of the non-pile-up portion of the previous pulse as an input parameter to acquire a pulse amplitude of the previous pulse after occurrence of the pile-up, and updating the pulse amplitude in accordance with a pulse falling edge attenuation principle at each sampling moment;

d. during digital integration of a subsequent pulse, subtracting a currently updated amplitude value of the previous pulse at each sampling moment to obtain an actual amplitude of the subsequent pulse; and e. if a next MVT trigger signal is received in the digital integration time of the subsequent pulse, treating the subsequent pulse as the previous pulse to iteratively perform the above processes.

In order to realize the above object, in the disclosure the following technical solution is provided:

A system for real-time processing of a pulse pile-up event, comprising:

a trigger module for generating an integration trigger signal upon arrival of an MVT trigger signal, and updating a sampled falling edge waveform of a previous pulse to a current baseline value;

a digital integration module for, upon receipt of the integration trigger signal, subtracting the baseline calibration value from an RTS sampled value as an actual pulse amplitude for integration;

a fitted energy value lookup module for presenting a fitted energy value of a non-integrated portion of pulses based on the current baseline value and the integration time; and a fitted baseline value lookup module for acquiring a non-sampled waveform amplitude of the previous pulse due to the pile-up based on the current baseline value and the integration time and treating the non-sampled waveform amplitude of the previous pulse as the baseline calibration value for a subsequent pulse.

In the aforesaid system for real-time processing of a pulse pile-up event, preferably, if a second MTV trigger signal does not occur in the digital integration module during a digital integration period, it is deemed that no pile-up event occurs, and an energy value of the pulse output upon completion of the digital integration period is an energy value of the pulse corresponding to the current MVT trigger signal.

In the aforesaid system for real-time processing of a pulse pile-up event, preferably, if a second MTV trigger signal occurs in the digital integration module during a digital integration period, the digital integral module is configured to add a fitted energy value of the non-integrated portion acquired by the fitted information lookup module to the energy value of the integrated portion prior to occurrence of the second MVT trigger signal as an energy value of the pulse corresponding to the current MVT trigger signal.

As can be seen from the above technical solutions, in the disclosure the method for real-time processing of a pulse pile-up event based on the MVT technique is proposed: firstly, the multi-voltage threshold sampling method is used to realize identification of the pile-up pulses at a high count rate and triggering of the pulse signal processing procedure, and then the priori information and the acquired pulse information are used for looking up the table to acquire information of the incorrectly sampled portion due to the pulse pile-up, so as to realize the real-time recovery of the pile-up pulse information. The method in the disclosure is simple and high-efficient, easy to be implemented on a real-time data acquisition system of a detector level, and is able to achieve an optimized recovery effect of pile-up pulse information at a low sampling rate.

BRIEF DESCRIPTION OF THE DRAWINGS

The accompanying drawings with reference to the embodiments or state of art will be described for the purpose of demonstrating the embodiments of the application and the state of art. It is apparent that the figures as shown are merely illustrative of some embodiments as recited in the disclosure. It should be understood by those skilled in the art that various alternatives to the figures as shown may be appreciated, without creative work involved.

FIG. 2 is a flowchart of the method for real-time processing of a pulse pile-up event according to the disclosure, wherein

DETAILED DESCRIPTION

A clear and comprehensive description of the embodied solutions of the disclosure will be set forth below with reference to the drawings accompanying to the description for better understanding of the invention by those skilled in the art. It is apparent that the embodiments as described herein are merely exemplary, but not exhausted. It should be understood that various alternatives to the embodiments described herein may be employed by those skilled in the art without departing from the spirit and scope of the invention.

In the disclosure, a method for real-time processing of a pulse pile-up event based on the Multi-voltage Threshold (abbreviated as MVT) technique is proposed. The method is simple and efficient, easy to be implemented on a real-time data acquisition system of a detector level, and is able to achieve an optimized recovery effect of pile-up pulse information at a low sampling rate.

It is typically said that Scintillation pulses are composed of a sharply rising edge and a falling edge of gentle slope, wherein the sharply rising edge contains time information of the pulse, while the amplitude variation of the entire pulse waveform contains energy information of the pulse. Since the rising edge of each pulse still remains intact in most pile-up events, the data acquisition system only needs to sample the rising edge of the pulse to determine whether the pulse appears or not and to obtain the corresponding time information. On the other hand, the waveforms of the scintillation pulses conform to a certain profile variation, such that for specific detectors and front-end electronics, the pulse mathematical model thereof is relatively constant, and information of the remaining non-sampled portion of the pulse can be derived from the acquired information of the sample point of the pulse. Therefore, the sharply rising edges may be sampled using the MVT digitization method to identify the presence or absence of the pulse and the arrival time. Then the falling edge of the pulse waveform is sampled to recover the incorrectly sampled pulse waveform due to the pulse pile-up, thereby realizing the identification and information recovery of the pile-up pulses.

Figure 1:
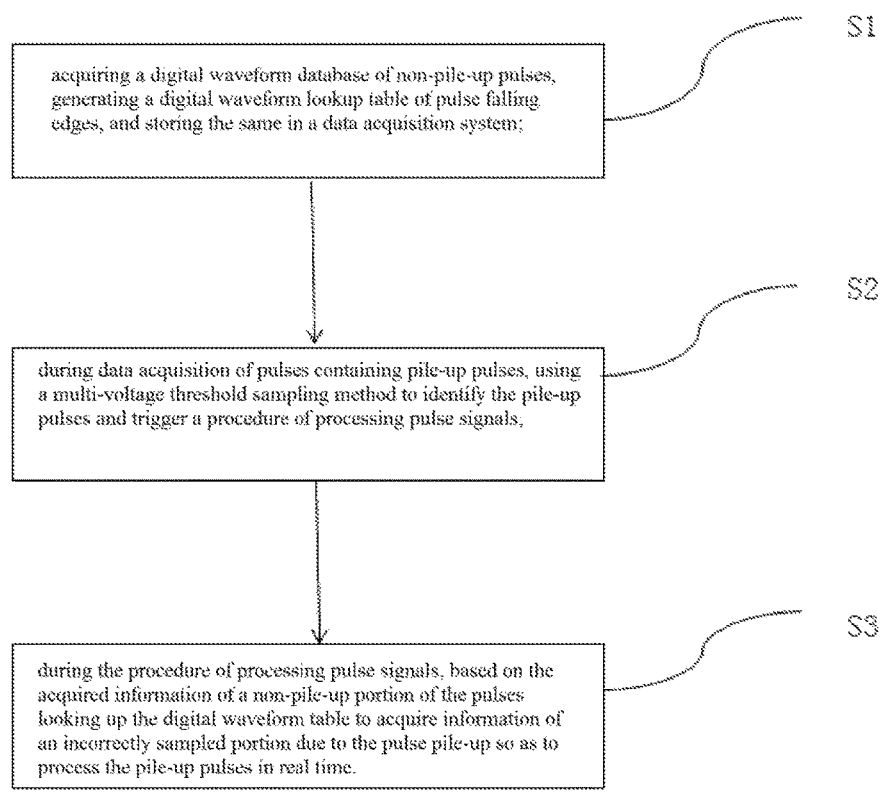
FIG. 1 is a schematic diagram illustrating the steps of the method for real-time processing of a pulse pile-up event according to the disclosure.

FIG. 1 is a schematic diagram of the steps of the method for real-time processing of a pulse pile-up event according to the disclosure. The method for real-time processing of a pulse pile-up event, comprising steps of:

S1: acquiring a digital waveform database of non-pile-up pulses, generating a digital waveform lookup table of pulse falling edges, and storing the same in a data acquisition system;

S2: during data acquisition of pulses containing pile-up pulses, using a multi-voltage threshold sampling method to identify the pile-up pulses and trigger a procedure of processing pulse signals; and S3: during the procedure of processing pulse signals, based on the acquired information of a non-pile-up portion of the pulses looking up the digital waveform table to acquire information of an incorrectly sampled portion due to the pulse pile-up so as to process the pile-up pulses in real time.

In the disclosure, the MVT method is proposed to identify the pile-up pulses. The MVT method realizes sampling of the rising edges of scintillation pulses at low cost and with high performance, and can be used for real-time identification of pulses in a pulse pile-up. In addition, this method provides synchronous trigger signals for the same gamma photon for the processing of multiple scintillation pulse angular signals generated in a position-sensitive detector, thereby improving the acquisition accuracy of the position information.

In the disclosure, the real-time processing of information of piled-up pulses is based on lookup tables. According to priori information of a pulse, a possible energy value and amplitude variation of a non-integrated portion are obtained in advance and written into lookup tables. The tables are looked up according to information of the sampled portion of a pulse during the process of real-time data acquisition, to obtain energy information of the incorrectly sampled portion of a previous pulse in the pile-up pulse, and energy effect of the previous pulse imposed to the subsequent pulse waveform after pulse pile-up.

The step S1 comprises steps of:

P1 in the case of non-pile-up pulses, using the multi-voltage threshold sampling method as a trigger signal of acquiring normal pulses;

P2 after triggering, sampling the pulse waveforms by a RTS method to acquire scintillation pulse digital waveforms;

P3 extracting amplitude variation of falling edge of each scintillation pulse in a database of scintillation pulse digital waveforms, and generating a respective lookup table of fitted baseline values and a respective lookup table of fitted energy values; and P4 storing the tables in the data acquisition system.

The step S2 comprises steps of:

P1 acquiring scintillation pulse electrical signals at a high count rate by the data acquisition system, two or more of the scintillation pulses that are excessively adjacent to each other being subject to a pulse pile-up due to a duration of the scintillation pulses and their indefinite occurrence time;

P2 sampling the scintillation pulse electrical signals respectively by an MVT method that performs a voltage comparison of sharply rising edges of the scintillation pulse waveforms with a plurality of voltage thresholds, wherein no matter whether the pulses are pile-up pulses or not, level switching signals can be acquired at the rising edges thereof; and P3 using the level switching signals acquired by the MVT method as identification signals for the pulses to trigger sampling of the pulses with an RTS method and digital integration of the pulses to acquire energy information of the pulses.

The step S3 specifically comprises steps of:

a. during sampling data at the high count rate by the data acquisition system, in the case of occurrence of a pile-up event, using a previous MVT trigger signal as a start signal for digital integration of a previous pulse;

b. upon occurrence of a second MVT trigger signal, using the pulse falling edge of the non-pile-up portion of the previous pulse in the pile-up pulses as an input parameter to look up the lookup table of fitted energy values to acquire an energy value of the pile-up portion of the previous pulse, and adding the latter to the acquired energy value of the non-pile-up portion as an energy value of the previous pulse;

c. meanwhile using the pulse falling edge of the non-pile-up portion of the previous pulse as an input parameter to look up the lookup table of fitted baseline values to acquire a pulse amplitude of the previous pulse after occurrence of the pile-up, and updating the pulse amplitude in accordance with a pulse falling edge attenuation principle at each sampling moment;

d. during digital integration of a subsequent pulse, subtracting a currently updated amplitude value of the previous pulse at each sampling moment to obtain an actual amplitude of the subsequent pulse; and e. if a next MVT trigger signal is received in the digital integration time of the subsequent pulse, treating the subsequent pulse as the previous pulse to iteratively perform the above processes.

Figure 2A:
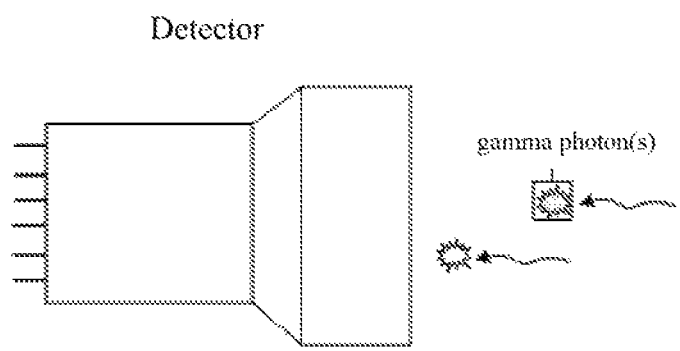
FIG. 2(a) is a schematic diagram of two gamma photons entering a detector unit successively.

As shown in FIG. 2, the specific embodiments according to the disclosure is proposed. FIG. 2 is a flowchart of the method for real-time processing of a pulse pile-up event based on the multi-voltage threshold sampling technique. The occurrence of a pile-up event and the processing procedure are as follows:

FIG. 2(a): Two gamma photons 200 successively enter a detector unit 100 in a relatively short interval.

Figure 2B:
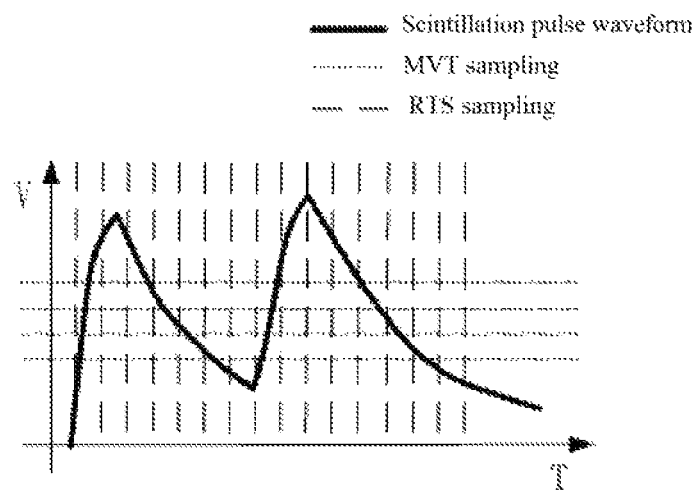
FIG. 2(b) is a schematic diagram of sampling the scintillation pulse electrical signals by an MVT method and an RTS method respectively.

FIG. 2(b): The detector may covert the gamma photons into scintillation pulse electrical signals. Two scintillation pulses that are excessively adjacent to each other are subject to a pulse pile-up due to a duration thereof. The scintillation pulse electrical signals are sampled by an MVT method and an RTS method respectively, wherein the MVT method performs a voltage comparison of the sharply raising edge of the pulse waveform with voltage threshold(s) to obtain level switching signals, and the RTS method performs continuous sampling of voltage at fixed time intervals.

Figure 2C:
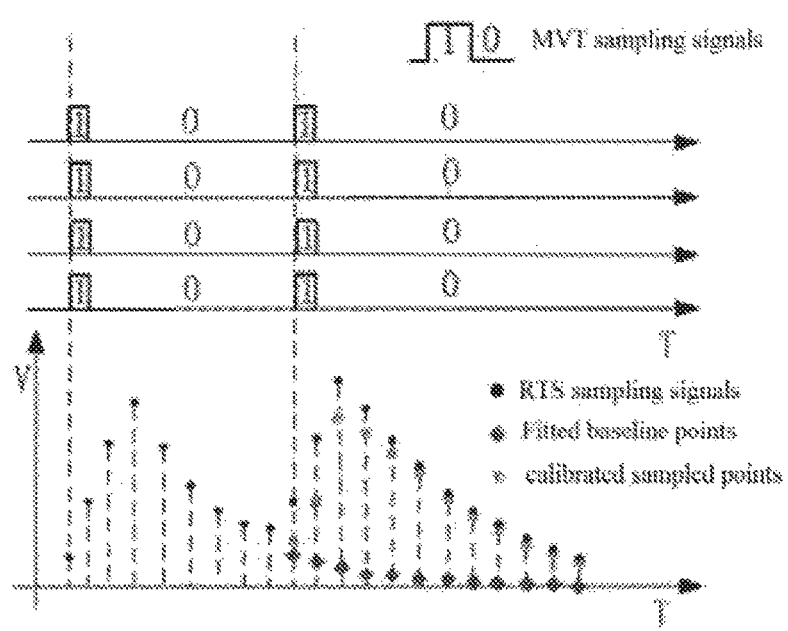
FIG. 2(c) is a schematic diagram of using the level switching signals obtained by the MVT method as the trigger signals for indicating occurrence of the pulses, using the voltage sample points obtained by the RTS method for digital integration to obtain the pulse energy, in order to obtain information of each pulse in the pile-up event.

FIG. 2(c): The level switching signals acquired by the MVT method are used as trigger signals for a pulse occurrence, and the voltage sample points acquired by the RTS method are used for digital integration to obtain pulse energy, so as to obtain information of each pulse in the pile-up event. The specific process is as follows:

a. acquiring a digital waveform database of non-piled-up pulses at a low count rate by a data acquisition system, generating a lookup table of fitted baseline value and a lookup table of fitted energy values of the pulse falling edges, and storing the tables in the data acquisition system;

b. during sampling data at the high count rate by the data acquisition system, in the case of occurrence of a pile-up event, using a previous MVT trigger signal as a start signal for digital integration of a previous pulse;

c. upon occurrence of a second MVT trigger signal, using the pulse falling edge of the non-pile-up portion of the previous pulse in the pile-up pulses as an input parameter to look up the lookup table of fitted energy values to acquire an energy value of the pile-up portion of the previous pulse, and adding the latter to the acquired energy value of the non-pile-up portion as an energy value of the previous pulse;

d. meanwhile using the pulse falling edge of the non-pile-up portion of the previous pulse as an input parameter to look up the lookup table of fitted baseline values to acquire a pulse amplitude of the previous pulse after occurrence of the pile-up, and updating the pulse amplitude in accordance with a pulse falling edge attenuation principle at each sampling moment;

e. during digital integration of the subsequent pulse, subtracting a corresponding amplitude value of the previous pulse at each sampling moment to obtain an actual amplitude of the subsequent pulse; and f. if a next MVT trigger signal is received in the digital integration time of the subsequent pulse, treating the subsequent pulse as the previous pulse to iteratively perform the above processes.

Figure 3:
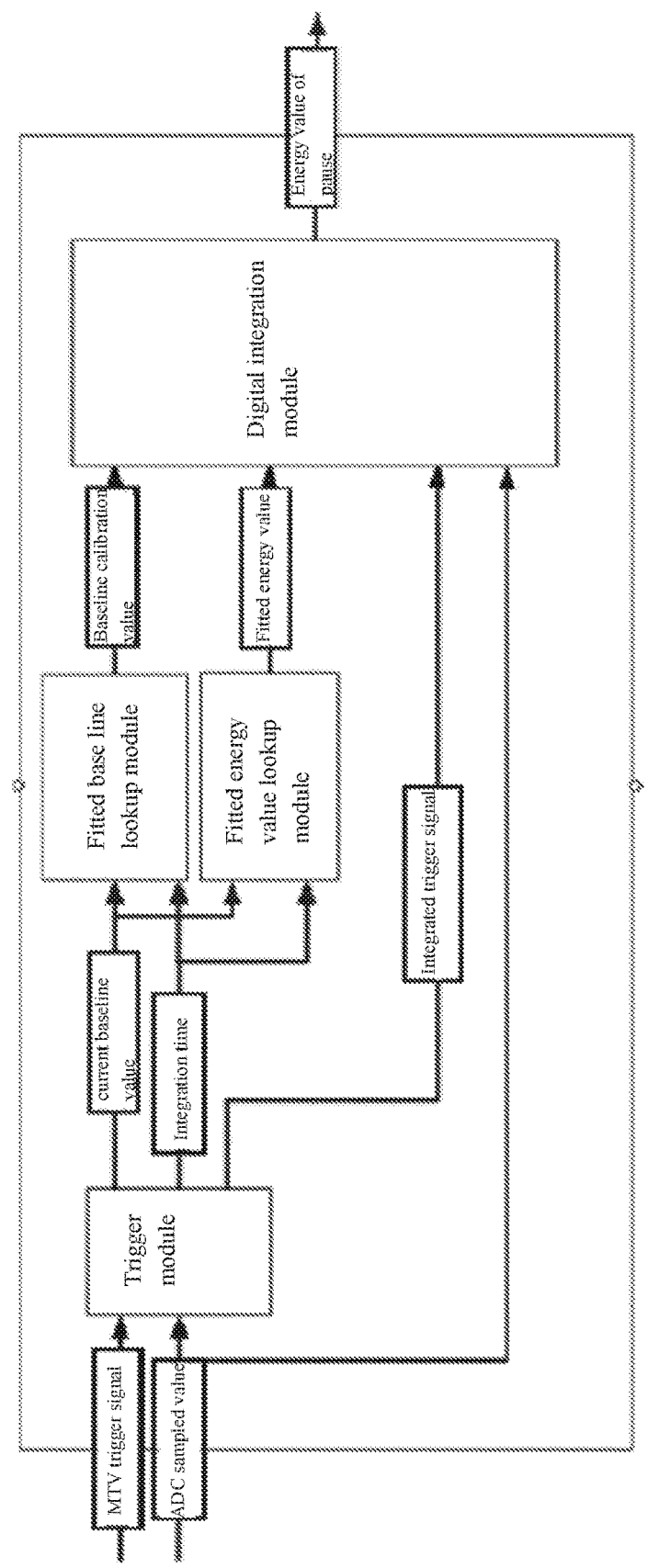
FIG. 3 is a schematic diagram of an embodied framework of the method for real-time processing of a pulse pile-up event in a detector according to the disclosure.

The embodiment of implementing the method according to the disclosure in a detector is as shown in FIG. 3, i.e., the system for real-time processing of a pulse pile-up event according to the disclosure, comprising:

a trigger module for generating an integration trigger signal upon arrival of an MVT trigger signal, and updating a sampled information of a previous pulse;

a digital integration module for, upon receipt of the integration trigger signal, subtracting the baseline calibration value from an RTS sampled value as an actual pulse amplitude for integration, wherein if a second MTV trigger signal does not occur in the digital integration module during a digital integration period, it is deemed that no pile-up event occurs, and an energy value of the pulse output upon completion of the digital integration period is an energy value of the pulse corresponding to the current MVT trigger signal, and wherein if a second MTV trigger signal occurs in the digital integration module during a digital integration period, the digital integral module is configured to add a fitted energy value of the non-integrated portion acquired by the fitted information lookup module to the energy value of the integrated portion prior to occurrence of the second MVT trigger signal as an energy value of the pulse corresponding to the current MVT trigger signal;

a fitted energy value lookup module for presenting a fitted energy value of a non-integrated portion of pulses based on the current baseline value and the integration time; and a fitted baseline value lookup module for acquiring a non-sampled waveform amplitude of the previous pulse due to the pile-up based on the current baseline value and the integration time and treating the non-sampled waveform amplitude of the previous pulse as the baseline calibration value for a subsequent pulse.

Figure 4:
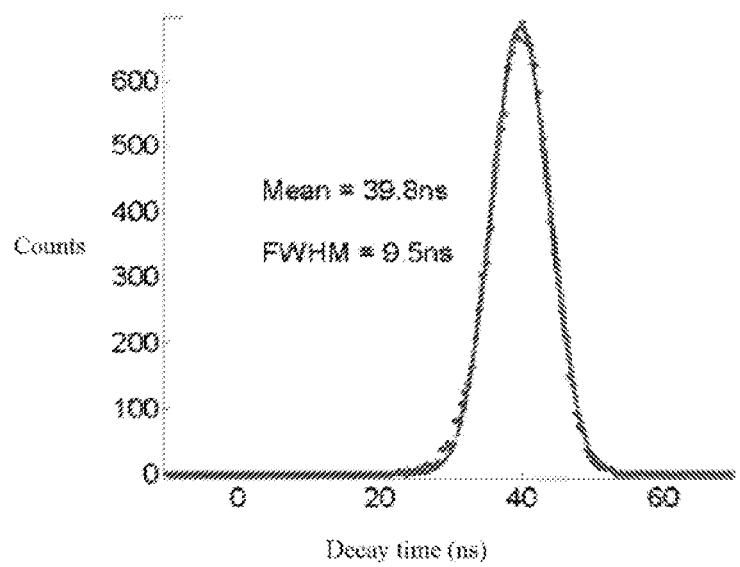
FIG. 4 is a schematic diagram of the decay time distribution of the falling edges of the scintillation pulses according to the method for real-time processing of a pulse pile-up event according to the disclosure.

Since waveforms of scintillation pulses conform to a profile variation, for particular detectors and front-end electronics, the pulse mathematical model is relatively constant. As shown in FIG. 4, after an exponentially decaying fitting of the digital waveform sampled points of the falling edges of the scintillation pulses, the distribution of the attenuation constants approximately conforms to a specific value profile. Thus, based on all the possible sampled points and amplitudes of the falling edges of the scintillation pulses, the amplitudes of the corresponding remaining non-sampled points and the sum of energy can be calculated according to the exponential decay equation of the falling edges and can be written respectively into the fitted baseline value lookup module and the fitted energy value lookup module. The amplitude variation and energy information of the non-sampled pulses can be obtained in real time by inputting the sampled points and amplitudes as addresses into the above lookup tables during actual data acquisition.

Compared with the state of art, the advantages of the disclosure include:

1. The MVT digitization method quickly and accurately samples rising edges of scintillation pulses output from a detector, and can recognize in real time the occurrence time of each pulse in a pile-up pulse.

2. When the MVT digitization method is applied for processing of a pulse pile-up in a position-sensitive detector, the summed-up scintillation pulse signals generated by gamma photons can be sampled to achieve simultaneous sampling and processing of multiple position signals generated by total signals, facilitating accurately obtaining the ratio of each position signals to obtain position information.

3. Since possible energy values and amplitude changes of a non-integrated portion of scintillation pulses are determined in advance in accordance with a scintillation pulse model in certain detectors and front-end electronics, and stored in detector hardware in the form of lookup tables, corresponding results can be quickly obtained by looking up the tables according to information of the sampled pulse in the actual data sampling process, without the need of complicated calculation of pulse fitting equation, thereby realizing a real-time and high-throughput processing of pile-up pulses.

4. An iterative processing flow for two or more consecutively arriving piled-up pulses is realized. Besides, since the baseline calibration value is updated at the arrival of each pulse regardless of whether there is a pulse pile-up, it is possible to process the pluses with the time interval between the two pulses greater than the integration period but the falling edge amplitude of the previous pulse that affects the acquisition of the information of a subsequent pulse.

In the method and system according to the disclosure, the scintillation crystals used in the PET detector may be of any material that can convert gamma photons into visible light photons, such as lutetium yttrium silicate scintillation crystal (abbreviated as LYSO), bismuth germanate crystal (abbreviated as BGO), scintillation crystal gadolinium silicate scintillation crystal (abbreviated as GSO), or the like. The photodetector used in a PET detector may be of any device that can convert the visible light signals into scintillation pulse electrical signals, such as a PMT, a Silicon Photomultiplier (abbreviated as SiPM), or the like. The pulse energy information acquisition method may be of an RTS type sampling method such as an ADC method, or a voltage domain sampling method such as a MVT method, a Time Over Threshold (TOT) method, or the like. The method of obtaining an energy value and an amplitude variation of a non-sampled portion according to information of a sampled portion of a pulse may be of methods such as exponential fitting of pulse falling edge, a pulse fractional integral value ratio or the like.

It is to be understood that the scope of the present invention is exemplary, but not to be interpreted as limited to the specific embodiments disclosed herein. As will be appreciated by those skilled in the art, changes and variations to the invention are considered to be within the ability of those skilled in the art. Such changes and variations are intended by the inventors to be within the scope of the invention.

What is claimed is:

1. A method for real-time processing of a pulse pile-up event, characterized by comprising steps of:
    S1: acquiring a digital waveform database of non-pile-up pulses, generating a digital waveform lookup table of pulse falling edges, and storing the same in a data acquisition system;
    S2: during data acquisition of pulses containing pile-up pulses, using a multi-voltage threshold sampling method to identify the pile-up pulses and trigger a procedure of processing pulse signals; and
    S3: during the procedure of processing pulse signals, based on the acquired information of a non-pile-up portion of the pulses looking up the digital waveform table to acquire information of an incorrectly sampled portion due to the pulse pile-up so as to process the pile-up pulses in real time.

2. The method for real-time processing of a pulse pile-up event according to claim 1, characterized in that the step S1 comprises steps of:
    P1: in the case of non-pile-up pulses, using the multi-voltage threshold sampling method as a trigger signal of acquiring normal pulses;
    P2: after triggering, sampling the pulse waveforms by an RTS method to acquire scintillation pulse digital waveforms;
    P3: extracting amplitude variation of falling edge of each scintillation pulse in a database of scintillation pulse digital waveforms, and generating a respective lookup table of fitted baseline values and a respective lookup table of fitted energy values; and
    P4: storing the tables in the data acquisition system.

3. The method for real-time processing of a pulse pile-up event according to claim 1, characterized in that the step S2 comprises steps of:
    P1: acquiring scintillation pulse electrical signals at a high count rate by the data acquisition system, two or more of the scintillation pulses that are excessively adjacent to each other being subject to a pulse pile-up due to a duration of the scintillation pulses and their indefinite occurrence time;

P2: sampling the scintillation pulse electrical signals respectively by an MVT method that performs a voltage comparison of sharply rising edges of the scintillation pulse waveforms with a plurality of voltage thresholds, wherein no matter whether the pulses are pile-up pulses or not, level switching signals is able to be acquired at the rising edges thereof; and P3: using the level switching signals acquired by the MVT method as identification signals for the pulses to trigger sampling of the pulses with an RTS method and digital integration of the pulses to acquire energy information of the pulses.

4. The method for real-time processing of a pulse pile-up event according to claim 1, characterized in that the step S3 comprises steps of:

a: during sampling data at the high count rate by the data acquisition system, in case of occurrence of a pile-up event, using a previous MVT trigger signal as a start signal for digital integration of a previous pulse;

b: upon occurrence of a second MVT trigger signal, using the pulse falling edge of the non-pile-up portion of the previous pulse in the pile-up pulses as an input parameter to look up the lookup table of fitted energy values to acquire an energy value of the pile-up portion of the previous pulse, and adding the acquired energy value of the pile-up portion to the acquired energy value of the non-pile-up portion as an energy value of the previous pulse;

c: meanwhile using the pulse falling edge of the non-pile-up portion of the previous pulse as an input parameter to look up the lookup table of fitted baseline values to acquire a pulse amplitude of the previous pulse after occurrence of the pile-up, and updating the pulse amplitude in accordance with a pulse falling edge attenuation principle at each sampling moment;

d: during digital integration of a subsequent pulse, subtracting a currently updated amplitude value of the previous pulse at each sampling moment to obtain an actual amplitude of the subsequent pulse; and e: if a next MVT trigger signal is received in the digital integration time of the subsequent pulse, treating the subsequent pulse as the previous pulse to iteratively perform the above processes.

5. A system for real-time processing of a pulse pile-up event, characterized by comprising:

a trigger module for generating an integration trigger signal upon arrival of an MVT trigger signal, and updating a sampled falling edge waveform of a previous pulse to a current baseline value;

a digital integration module for, upon receipt of the integration trigger signal, subtracting the baseline calibration value from an RTS sampled value as an actual pulse amplitude for integration;

a fitted energy value lookup module for presenting a fitted energy value of a non-integrated portion of pulses based on the current baseline value and the integration time; and a fitted baseline value lookup module for acquiring a non-sampled waveform amplitude of the previous pulse due to the pile-up based on the current baseline value and the integration time and treating the non-sampled waveform amplitude of the previous pulse as the baseline calibration value for a following pulse.

6. The system for real-time processing of a pulse pile-up event according to claim 5, characterized in that if a second MTV trigger signal does not occur in the digital integration module during a digital integration period, it is deemed that no pile-up event occurs, and an energy value of the pulse output upon completion of the digital integration period is an energy value of the pulse corresponding to the current MVT trigger signal.

7. The system for real-time processing of a pulse pile-up event according to claim 5, characterized in that if a second MTV trigger signal occurs in the digital integration module during a digital integration period, the digital integral module is configured to add a fitted energy value of the non-integrated portion acquired by the fitted information lookup module to the energy value of the integrated portion prior to occurrence of the second MVT trigger signal as an energy value of the pulse corresponding to the current MVT trigger signal.

* * * * *